United States Patent [19]

Nakahata et al.

[11] Patent Number: 4,872,187

[45] Date of Patent: Oct. 3, 1989

[54] X-RAY TOMOGRAPHIC IMAGING SYSTEM AND METHOD

[75] Inventors: Kozo Nakahata, Chigasaki; Toshimitsu Hamada, Yokohama; Yasuo Nakagawa, Chigasaki; Mineo Nomoto, Yokohama, all of Japan

[73] Assignee: Hitachi, Ltd., Tokyo, Japan

[21] Appl. No.: 156,179

[22] Filed: Feb. 16, 1988

[30] Foreign Application Priority Data

Feb. 27, 1987 [JP] Japan ............................. 62-42535
Apr. 20, 1987 [JP] Japan ............................. 62-95147
Jun. 10, 1987 [JP] Japan ............................. 62-143103

[51] Int. Cl.$^4$ ............................................. G01B 15/06
[52] U.S. Cl. ............................................. 378/4; 378/20; 378/58; 378/17
[58] Field of Search ............... 378/4, 17, 19, 20, 21, 378/22, 58

[56] References Cited

U.S. PATENT DOCUMENTS 4,164,657 8/1979 Duinker et al. ............. 378/19
4,691,332 9/1987 Burstein ....................... 378/17

FOREIGN PATENT DOCUMENTS 54-143290 of 1979 Japan ............................ 378/58

Primary Examiner—Craig E. Church
Attorney, Agent, or Firm—Kenyon & Kenyon

[57] ABSTRACT

In an X-ray tomographic imaging system and method, an object to be inspected is irradiated with X-rays from an X-ray source to obtain an X-ray transmission image of the object. The X-ray transmission image is converted by an X-ray fluorescence image intensifier into a detection image. The intensity of the detection image is also intensified by the X-ray fluorescence image intensifier. A photo-electric converter converts the intensified detection image from the X-ray fluorescence image intensifier into an electrical signal. The object to be inspected is held by an object holder rotatably at a position in proximity to the X-ray source and movably in a direction of the axis of rotation of the object and a direction perpendicular to the rotation axis. The electrical signal from the photo-electric converter is processed to a cross-sectional image.

14 Claims, 11 Drawing Sheets

FIG. 13a
FIG. 13b
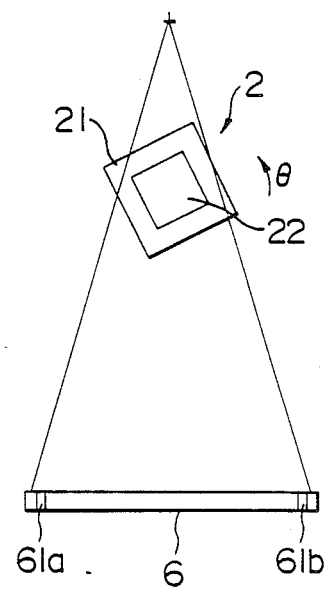
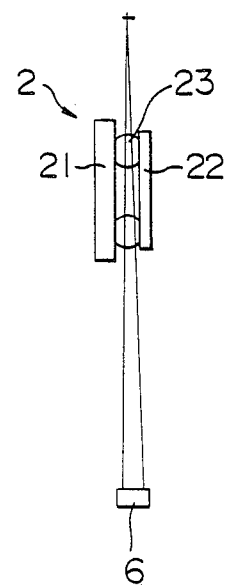

X-RAY TOMOGRAPHIC IMAGING SYSTEM AND METHOD

BACKGROUND OF THE INVENTION

The present invention relates to an X-ray tomographic imaging technique, and more particularly to an X-ray tomographic imaging system and method suitable for the inspection of minute defects in industrial parts, more especially, the inspection of defects in soldered portions between an electronic circuit module and a printed circuit board.

A typical example of the conventional industrial CT (computed tomography) apparatus is disclosed by Nakamura, "Industrial X-ray CT scanner and its applications", Keisoh, Vol. 27, No. 2, (1984), pp. 48–51. The disclosed apparatus includes an X-ray source which has a relatively larger size as compared with an object to be inspected and a multichannel array of X-ray detectors each of which contains a Xenon (Xe) gas filled therein and has its width of 1 to 2 mm. Usually, the detector array has 300 to 500 channels. By irradiating the object to be inspected with X-rays emitted in a sector shape from the X-ray source while rotating the object around its own axis, the intensities of X-rays transmitted through the object from the entire peripheral directions are detected by the X-ray detector array so that the detected data are used to reconstruct a cross-sectional image of the object to be inspected. However, the resolving power of this apparatus for the object to be inspected is on the order of 300 $\mu m^\phi$. Therefore, it was impossible to inspect relatively minute portions such as soldered portions at which an electronic circuit module and a printed circuit board are connected.

Another type of inspection apparatus using X-rays is disclosed by Tanimoto, "Recent non-destructive inspection techniques", in "Pipe Arrangement and Apparatus", Vol. 25, No. 3 (1985), pp. 54–60. In the disclosed X-ray TV (television) apparatus, internal defects of an object to be inspected non-destructively are inspected in superposition with images of those which are other than the object in question, by obtaining an internal image of the object from a mere X-ray transmission image or X-ray projection image which is acquired through the irradiation of the object with X-rays, and this is a problem in inspecting minute portions clearly. Further, when using the apparatus as X-ray CT scanner, there is a problem that the geometrical distortion of an X-ray inspection image produced by an X-ray fluorescence image intensifier and/or a variation in intensity of irradiation X-rays construct a factor of operation errors, thereby resulting in an obstacle in reconstructing the shape of a cross section of the object with a high precision.

SUMMARY OF THE INVENTION

An object of the present invention is to provide an X-ray tomographic imaging system and method capable of inspecting minute portions such as soldered portions, more particularly, detecting a cross-sectional image with a high resolution.

Main components of an X-ray tomographic imaging system according to the present invention includes an X-ray source of minute spot size, an image intensifier having a function of converting an X-ray image into a visible image while enhancing the intensity of visible light, a charge storage type of linear image sensor for converting an output image of the image intensifier into an electrical signal, an object or specimen holder for holding an object to be inspected rotatably at a position in proximity to the X-ray source and movably in a direction of the axis of rotation of the object and a direction perpendicular to the rotation axis, and electrical circuit and calculating means for properly detecting and processing the electrical signal representative of the output image of the image intensifier.

The imaging system may include a light path changing-over mechanism for introducing the two-dimensional output image of the image intensifier into an image pick-up tube.

The image intensifier is used for visualizing the X-ray image and intensifying the visualized image. However, any converting means may be used which has a function capable of detecting the converted image of the X-ray image by a linear image sensor or image pick-up tube and making the converted image an image of wavelength which can be converted into an electrical signal, even if the converted image has, a wavelength spectrum distribution in an ultraviolet or infrared region.

By holding the object in proximity to the X-ray source with a minute spot size and properly selecting the position of the image intensifier, there can be obtained an X-ray transmission image in which a portion of the object to be inspected is projected in an enlarged form.

The use of an optical detection system composed of the image intensifier and the charge storage type of linear image sensor permits a high sensitivity, a wide dynamic range and a high resolution.

Since the two dimensional image can be monitored by the image pick-up tube, there can be realized an initial positioning which allows the precise irradiation of a minute interest portion of the object with the X-rays.

In one aspect of the present invention, the X-ray tomographic imaging system comprises a position adjusting mechanism for moving the rotation axis of the object to be inspected itself to a three-dimensional direction and adjusting the inclination or tilt angle of the rotation axis, the object being supported by the position adjusting mechanism, light path changing-over means disposed in a light path between an X-ray fluorescence image intensifier and the linear image sensor which can take in at least a one-dimentional image, monitor display means including an image pick-up tube and a monitor TV for displaying a monitor image of the two-dimensional X-ray image of the object, detection position displaying means for displaying a detection position of the linear image sensor on the monitor TV by means of a cursor, adjusting means for adjusting the detection position of the linear image sensor, and control means for performing a remote control of the adjusting means and adjusting a position of the cursor to be displayed on the monitor TV in an interlocking manner with the movement of the linear image sensor, whereby the adjustment and setting of the position of a cross section of the object to be imaged can be accurately and easily made even if the object is very small.

More particularly, the object to be inspected is irradiated with X-rays outputted from a minute spot size from the X-ray source having a small X-ray emission hole so that an X-ray image of the object is provided in a geometrically enlarged projection form. The X-ray image of the object is converted into a visible image by the X-ray fluorescence image intensifier having a function of intensifying the amount of light. The visible image is focused on a detection or X-ray receiving surface of the charge storage type of linear image sensor which can take in at least one-dimensional image. The use of the linear image sensor makes a small pixel size and a wide dynamic range possible. As a result, the detection can be made with a high sensitivity and a high resolution.

The visible image obtained by the X-ray florescence image intensifier is introduced into the image pick-up tube by the light path changing-over means so that the visible image is taken in the image pick-up tube in order to display a monitor image of the two-dimensional image of the object.

The detection position displaying means is provided for displaying the detection position of the linear image sensor on the monitor TV by means of the cursor. Thereby, it is possible to confirm the detection position of the linear image sensor for the set position and posture of the object.

When the shape of a cross section of the object is reconstructed by the X-ray tomographic imaging system, the object is rotated around its own axis. By moving the rotation axis of the object to a forward and backward direction (X direction) and a right and left direction (Y direction) through the position adjusting mechanism while observing an image displayed on the monitor TV, the positioning between the object and the linear image sensor is effected. Further, it is possible to adjust the detection magnification of the X-ray image by moving the rotation axis of the object to a height direction (Z direction) through the position adjusting mechanism while observing the image displayed on the monitor TV. Also, it is possible to set the inclination or tilt of the object to an optimum angle by adjusting the inclination angle Δ of the rotation axis of the object through the position adjustment mechanism.

Furthermore, by adjusting the rotation angle α of the detection position of the linear image sensor to set the detection position, it is possible to adjust the angle for a position at which a one-dimensional X-ray image of the object is to be taken in.

Since the position of the cursor indicative of the detection position of the linear image sensor and displayed on a screen of the monitor TV is adjusted interlocking with the movement of the linear image sensor by the control means, the detection position and posture of the object and a relation between the detection position of the object and the detection position of the linear image sensor can be adjusted through observation by the monitor TV, the adjustment and setting of the position of a cross section of the object to be imaged can be accurately and easily performed.

In an X-ray tomographic imaging system according to another aspect of the present invention, the distortion of an image detected by a detector s preliminarily measured for use as correction data. Upon detection of an X-ray image of the object, the intensity of X-rays with which the object is irradiated is detected through the monitor to correct data of the detected X-ray image of the object. As a result, any geometrical distortion of the X-ray inspection image produced by the X-ray fluorescence image intensifier and any variation in intensity of the irradiation X-ray can be corrected.

More particularly, an X-ray image of a scale provided with a multiplicity of slit-like graduations on an X-ray shielding plate is preliminarily detected through the irradiation of the scale with X-rays and data of the detected image are stored in a scale image memory.

Upon detection of an X-ray image of the object, the scale image data of the coordinate positions of the inspection image data are read from the scale image memory for correcting any geometrical distortion of an X-ray inspection image by the X-ray fluorescence image intensifier.

Upon detection of the X-ray image of the object, the intensity of X-rays directly entering the detector without passing through the object is also detected. When the shape of a cross section of the object is reconstructed, the detected intensity data are used as data for correction of the variation in intensity of irradiation X-rays.

BRIEF DESCRIPTION OF THE DRAWINGS

FIGS. 13a and 13b are views for explaining a geometrical position relation between an object to be inspected and a detector.

DESCRIPTION OF THE PREFERRED EMBODIMENTS

Embodiments of the present invention will now be explained by virtue of the accompanying drawings.

Figure 2A:
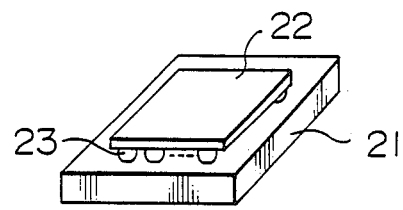
FIG. 2a is a perspective view showing an example of an object to be inspected.
Figure 2B:
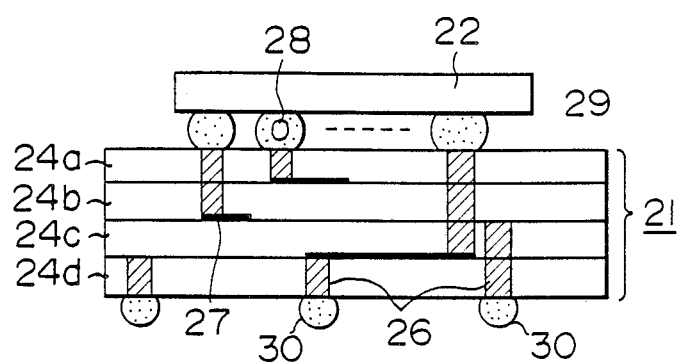
FIG. 2b is a partly enlarged cross-sectional view of the object to be inspected.
Figure 2C:
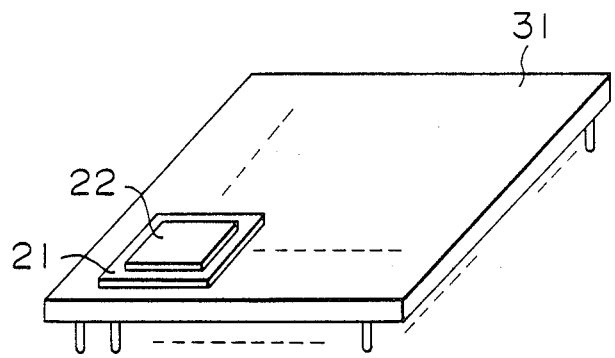
FIG. 2c is a perspective view showing a state in which a multiplicity of objects to be inspected are mounted on a mother substrate.

FIG. 2a shows an example of an LSI chip carrier as an object or specimen to be inspected. More particularly, an LSI chip 22 is mounted on a ceramic substrate 21 through CCB (controlled collapsed bonding) soldered portions 23. FIG. 2b shows an example of the structure of a cross section of the LSI chip carrier shown in FIG. 2a. The ceramic substrate 21 has a multilayer structure in which wiring layers 24a to 24d are laminated on each other. Each wiring layer has throughholes 26 filled with a metal material and circuit wirings 27 made of a metal material. The chip carrier is designed so that a multiplicity of such chip carriers can be mounted on a mother substrate 31 through solders 30 formed on the lower surfaces of the chip carriers, as is shown in FIG. 2c.

The present invention aims at the detection of defects such as bubbles 26 and bad shapes 29 which may be generated at the CCB soldered portions 33 of the LSI chip carrier, as is shown in FIG. 2b. For that purpose, an X-ray image from the entire peripheral direction of the side face of the chip carrier is detected to obtain a cross-sectional image of the soldered portions. Of course that the present invention is not limited to such an example but is applicable to an X-ray tomographic imaging inspection of electronic parts or the like with a resolution on the order of 50 $\mu m^\phi$.

Figure 1:
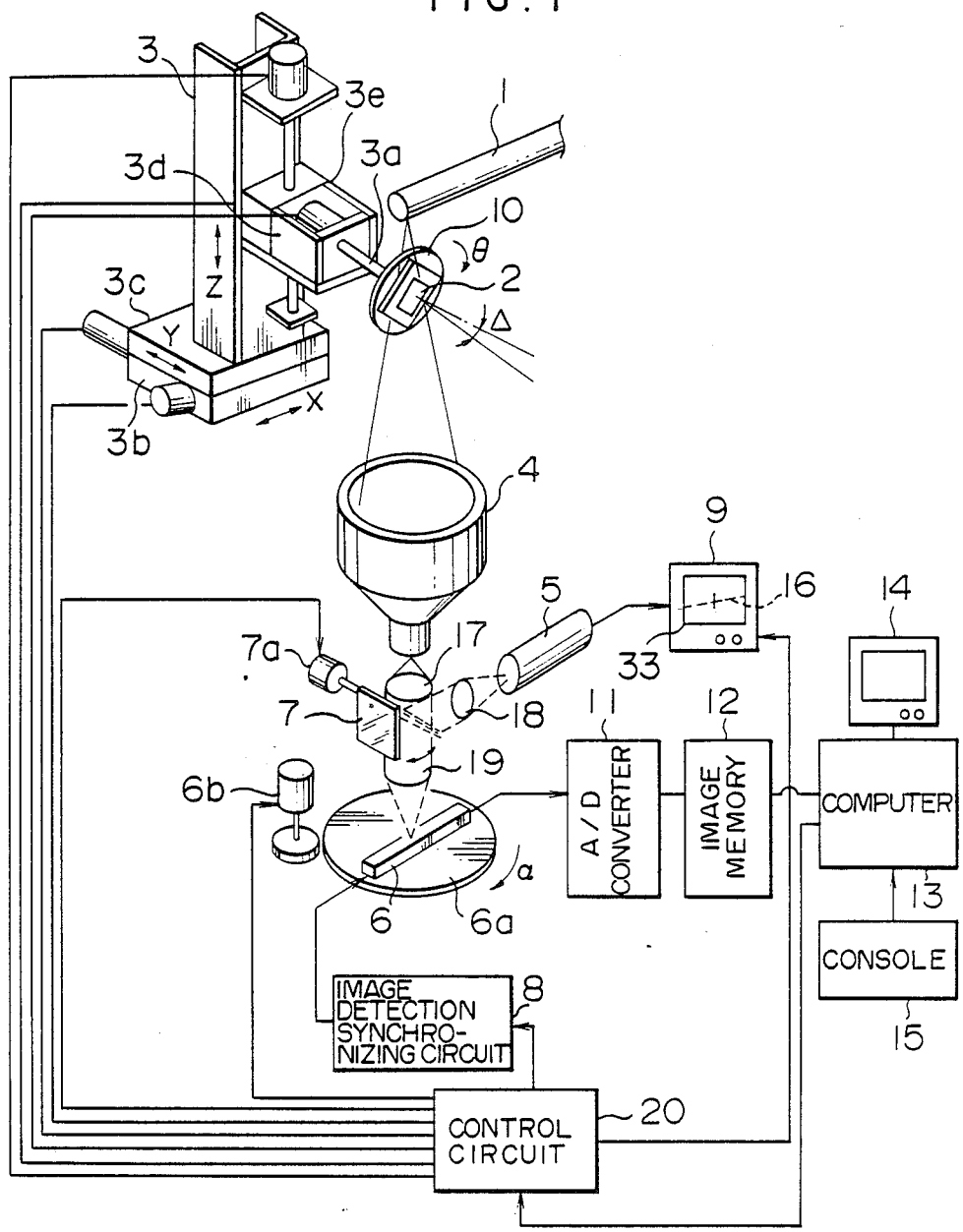
FIG. 1 is a perspective view showing the whole construction of an X-ray tomographic imaging system according to an embodiment of the present invention.

FIG. 1 is a perspective view showing the whole construction of an X-ray tomographic imaging system according to an embodiment of the present invention. Referring to FIG. 1, an object or specimen 2 to be inspected is held by an object or specimen holder 10. The object 2 is irradiated with a minute spot size of X-rays from an X-ray source 1 having a very small focus so that the object 2 is projected in an enlarged form onto an X-ray fluorescence image intensifier 4. The object holder 10 is mounted on a rotation shaft 3a as the rotation axis of the object itself which in turn is coupled to a position adjusting mechanism 3. The position adjusting mechanism 3 of the rotation shaft 3a includes an X stage 3b, a Y stage 3c, a Z stage 3d and a $\theta \cdot \Delta$ driving stage 3e and has a function of adjusting the position of the rotation shaft 3a in three dimensional (X, Y and Z) directions, a function of rotating the rotation shaft 3a in a direction of $\theta$ and a function of adjusting the inclination or tilt angle $\Delta$ of the rotation shaft 3a.

The X-ray fluorescence image intensifier 4 converts an image of X-rays transmitted through the object 2 into a visible image which in turn is focused onto a detection or X-ray receiving surface of an electron storage type of linear image sensor 6 through an optical system. The optical system includes lenses 17 and 18 interposed between the X-ray fluorescence image intensifier 4 and the linear image sensor 6.

The linear image sensor 6 is mounted on an $\alpha$ stage 6a. The visible image of the X-ray transmission image of the object 2 focused on the linear image sensor 6 is converted into a video signal by the linear image sensor 6. The video signal is delivered through an A/D converter circuit 11 and an image memory 12 to a computer 13 which performs an operation for reconstruction of a cross-sectional image of the object. The X-ray images detected by the linear image sensor 6 are sequentially quantized by the A/D converter circuit 11 and thereafter stored in the image memory 12. The data stored in the image memory 12 are read by the computer 13.

The $\alpha$ stage 6a of the linear image sensor 6 can be rotated in a direction of $\alpha$ in a horizontal plane by an $\alpha$ axis driving motor 6b for effecting the rotational adjustment of a one-dimensional image detection position for the object in the horizontal direction. The $\alpha$ axis driving motor 6b is connected to a control circuit 20 as a control means.

A mirror 7 as an optical path changing-over means is disposed in an optical path between the X-ray fluorescence intensifier 4 and the linear image sensor 6. The mirror 7 is coupled to a solenoid 7a so that the mirror 7 can be rotated by the solenoid 7a to effect the change-over of the optical path. A monitor display means is provided corresponding to the optical path changing-over mirror 7. The monitor display means includes a lens 18, an image pick-up tube 5 and a monitor TV 9 for effecting the observation of a two-dimensional X-ray image of the object 2. A detection position by the linear image sensor 6 can be displayed on the monitor TV 9 by means of a cursor 16 by a detection position displaying means (not shown).

At an initialization step, the detection position of the linear image sensor 6 and the position of the cursor on the monitor TV 9 are set so that they completely correspond to each other by adjusting the cursor display position upon fabrication of the system by use of a slit-like scale (not shown) placed on the X-ray fluorescence image intensifier 4. Thereafter, the cursor display position can be altered by the control circuit 20.

The initial positional adjustment for the X, Y and Z directions, $\Delta$ of the object holder 10 and $\alpha$ of linear image sensor 6 and the change-over of the optical path changing-over mirror 7 can be made through the computer 13 and the control circuit 20 in accordance with commands from a console 15 by an operator.

The control circuit 20 performs a remote control of the $\alpha$ axis driving motor 6b to control the amount of rotation of the o axis driving motor 6b and to adjust the inclination or tilt angle of the cursor 16 which is displayed on a screen of the monitor TV 9 corresponding to the detection position of the linear image sensor 6 in an interlocking manner with the rotation of the $\alpha$ axis driving motor 6b.

Figure 3:
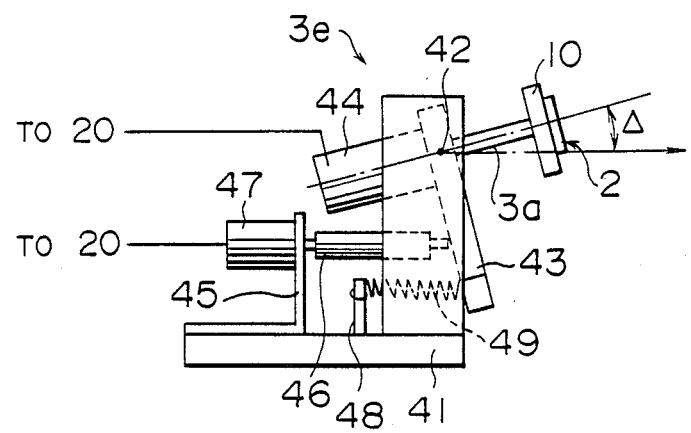
FIG. 3 is a side view of a θ·Δ driving stage of a rotation axis position adjusting mechanism in the embodiment shown in FIG. 1.

FIG. 3 is an enlarged side view of the $\theta \cdot \Delta$ driving stage 3e of the rotation axis position adjusting mechanism 3. The $\theta \cdot \Delta$ driving stage 3e shown in FIG. 3 includes a fixed support member 41 having a configuration of shape when viewed from the side face, an inclinational support member 43 supported inclinably at a vertical portion of the fixed support member 41 through a $\Delta$ rotatable fulcrum 42, a $\theta$ motor 44 mounted to the inclinational support member 43, a micrometer head 46 supported by a bracket 45 mounted on the fixed support member 41, a $\Delta$ motor 47 for rotating the micrometer head 46, and a tensile spring 49 stretched between the inclinational support member 43 and a spring bracket 48 mounted on the fixed support member 41.

By driving the $\theta$ motor 44, the rotation shaft 3a is rotated so that the object holder 10 having the object 2 held thereon is rotated in the $\theta$ direction.

When the $\Delta$ motor 47 is driven in a forward or reverse direction, the micrometer head 46 expands or contracts so that the inclinational support member 43 is rotated around the $\Delta$ rotatable fulcrum 42 in a direction in which the inclination angle $\Delta$ of the rotation shaft 4 supported by the inclinational support member 43 becomes larger or smaller.

Figure 4A:
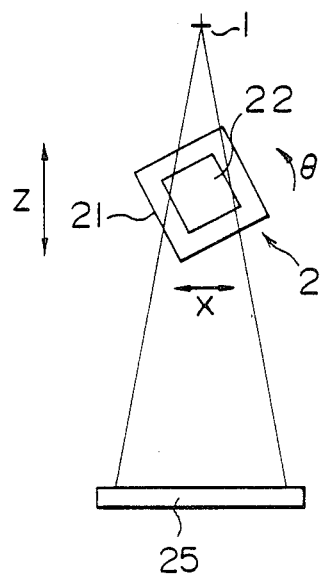
FIGS. 4a and 4b are front and side views showing an ideal position of the object when an X-ray image of the object is to be detected.
Figure 4B:
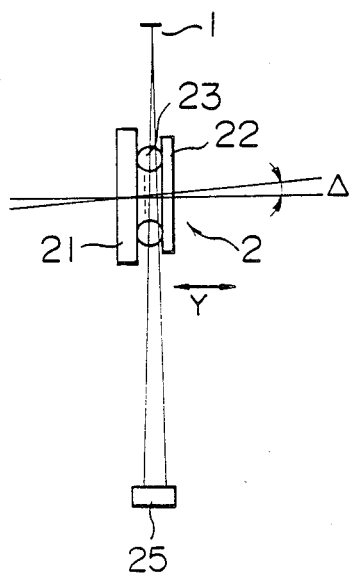

FIGS. 4a and 4b are front and side views of showing an ideal position of the object when detecting an X-ray image of the object. In order to obtain a highly precise X-ray or cross-sectional image of the CCB soldered portions 23 as the object to be inspected by rotating the CCB soldered portions in the $\theta$ direction to detect X-rays from the entire peripheral direction of the side face of the object, the positioning through the following adjustment is required. Namely, as shown in FIGS. 4a and 4b, the detection position of the object in the X and Y directions is first set and the object is thereafter moved in the Z direction to adjust the magnification of an X-ray image of the object. Also, the detection position 25 of the linear image sensor 6 is adjusted so that the detection position 25 is located parallel to the object in a plane of the drawing paper, as shown in FIG. 4a. Further, the inclination angle Δ is adjusted of the rotation shaft 3a of the object holder 10, as shown in FIG. 4b, in order to remove an error of the inclination of the rotation shaft 3a so that an X-ray image of the same cross section can be obtained for any rotation of the rotation shaft 3a in the θ direction. In FIGS. 4a and 4b, reference numeral 21 designates a ceramic substrate and numeral 22 designates an LSI chip.

Figure 5A:
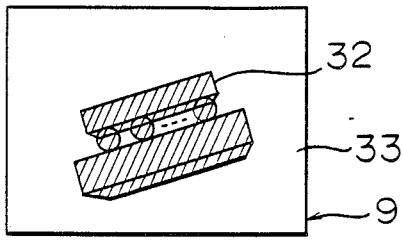
FIGS. 5a to 5d are views for explaining a procedure for the adjustment and setting of a detection position performed by use of the system shown in FIG. 1.
Figure 5B:
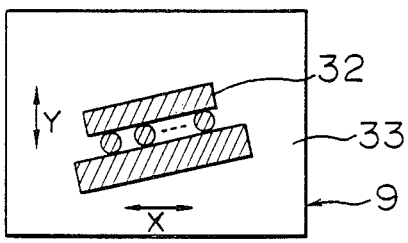
Figure 5C:
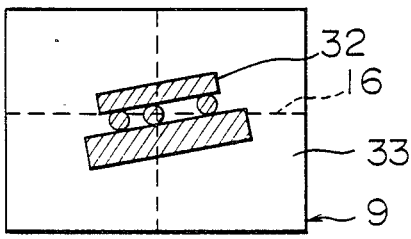
Figure 5D:
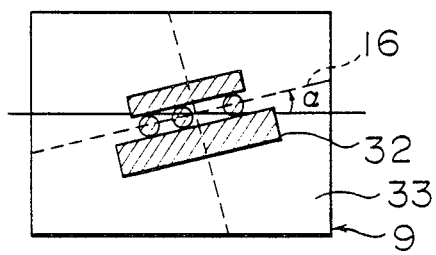

FIGS. 5a to 5d are views showing a procedure for performing the initial setting of the detection position while observing an X-ray image of the object by the monitor TV 9. Now assume that an initial state in which an X-ray image 32 of the object 2 is displayed on a screen 33 of the monitor TV 9, as shown in FIG. 5a. In accordance with a command from the console 15 by a key operation to correct the inclination angle Δ of the rotation shaft 3a, the Δ motor 47 is driven by the control circuit 20 to effect the correction of the inclination angle Δ of the rotation shaft 3a. A state after the correction is shown in FIG. 5b. Next, the cursor 16 indicative of a detection position of the linear image sensor 6 is displayed. And, in accordance with a command from the console 15 by a key operation to carry out the adjustment of the object 2 in the X and Y directions, motors for the X and Y stages 3b and 3c are driven by the control circuit 20 to move the object 2 in the X and Y directions, thereby setting the position of the object in the X and Y directions. Further, a motor for the Z stage 3d is driven by the control circuit 20 in accordance with a command from the console 15 by a key operation to move the object in the Z direction, thereby adjusting the magnification of the X-ray image 32. A state after the adjustment is shown in FIG. 5c. Next, a key operation for rotating the cursor 16 is carried out while paying attention to the inclination of the cursor 16. In accordance with a command from the console by such a key operation, the α axis driving motor 6b is driven by the control circuit 6b to rotate the α stage 6a. At the same time, the cursor 16 on the monitor TV 9 is rotated by the control circuit 20 by the same angle as the rotation angle of the α stage 6a. As a result, the correction of the rotation angle α of the linear image sensor 6 for the X and Y axes (or the position of the rotation direction of the cursor) is effected, as shown in FIG. 5d. In this manner, the adjustment and setting of the detection position for obtaining the X-ray image or cross-sectional image of the object 2 is terminated.

In this way, an initial positioning of the CCB soldered portion of the object 2 (see FIG. 1) to be inspected is performed. For this initial positioning purpose, the optical path changing-over mirror 7 is changed over to the side of monitor detection by the image pick-up tube 5 to display an X-ray transmission image of the portion of the object to be inspected on the monitor TV 9 (see FIGS. 5a to 5d). The position of the portion of the object to be inspected for X, Y, Δ and α is moved or adjusted so that the portion of the object to be inspected for the cursor 16 coincides with a position on the screen of the monitor TV 9 corresponding to the detection position of the linear image sensor 6. In this manner, the initial positioning can be easily made with a high precision.

Next, the optical path changing-over mirror 7 is changed over to the side of detection by the linear image sensor 6. The intensity of X-rays transmitted through the CCB soldered portions of the object 2 to be inspected is detected by the linear image sensor 6 as shown by the front and side views of FIGS. 4a and 4b while the object 2 is rotated by the driving mechanism 3 (see FIG. 1). The detection of the X-ray image by the linear image sensor 6 is effected by an image detection synchronizing circuit 8 for each predetermined rotation angle Δθ of the object holder 10 in the θ direction. Signals detected by the linear image sensor 6 are sequentially quantized by the A/D converter circuit 11 and stored into the image memory 12 to obtain data for the entire direction of θ=0°–360°.

Figure 6:
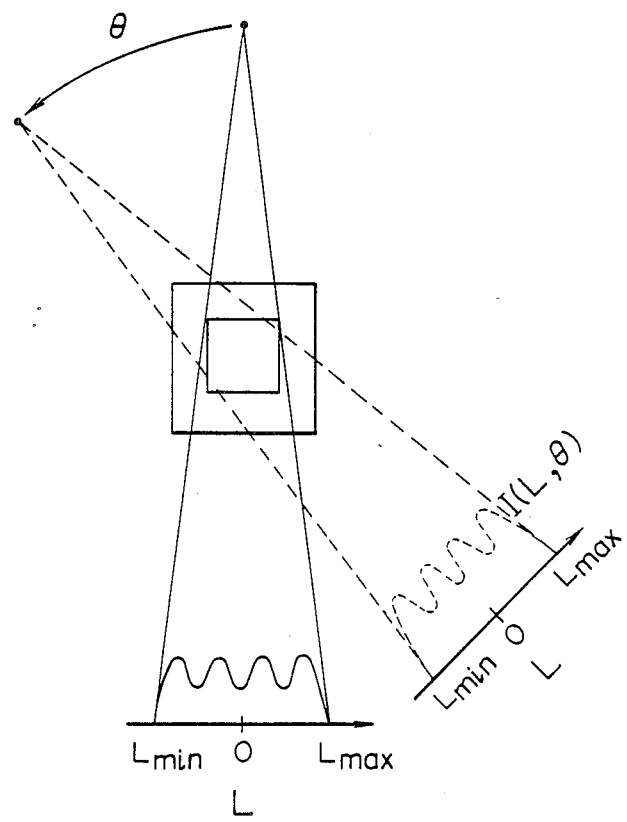
FIG. 6 is a view showing an example of X-ray image data detected by a linear image sensor.

FIG. 6 shows an example of a detection data function $I(L, θ)$ thus obtained corresponding to the each angular direction θ of the object 2, L representing a detection position on the linear image sensor. These detection data $I(L, θ)$ for the plurality directions are used for reconstructing the shape of a cross section of the CCB soldered portion by an operation processing by the computer 13 to display the reconstructed image on a display 14.

A data function $I(L, θ)$ of the intensity of transmitted X-rays detected by the linear image sensor is represented by the following equation:

$$I(L, θ) = I_0(L) \cdot e^{-\int \mu(x, y) dl} \tag{1}$$

wherein $\mu(x, y)$ is a function representative of the distribution of X-ray absorption coefficients of the object, $\int \mu(x, y) dl$ represents a linear integral of the X-ray absorption coefficient function $\mu(x, y)$ at passing positions of an X-ray beam, and $I_0(L)$ represents a function representative of the distribution of the intensities of irradiation X-rays. The equation (1) can be rewritten as follows:

$$\int \mu(x, y) dl = I_0(L)/I(L, θ) = P(L, θ). \tag{2}$$

$P(L, θ)$ represented by the equation (2) is projection data which is determined from the irradiation X-ray intensity distribution function $I_0(L)$ obtained by preliminarily detecting X-rays by the linear image sensor in the case where the object is not present.

The processing for reconstruction of the shape of a cross section includes determining the distribution of the X-ray absorption coefficient function $\mu(x, y)$ after the determination of the projection data function $P(L, θ)$ for each detection direction. Though various methods of determining the function $\mu(x, y)$ are known, a method using convolution will be briefly explained hereinunder as one example.

Figure 7:
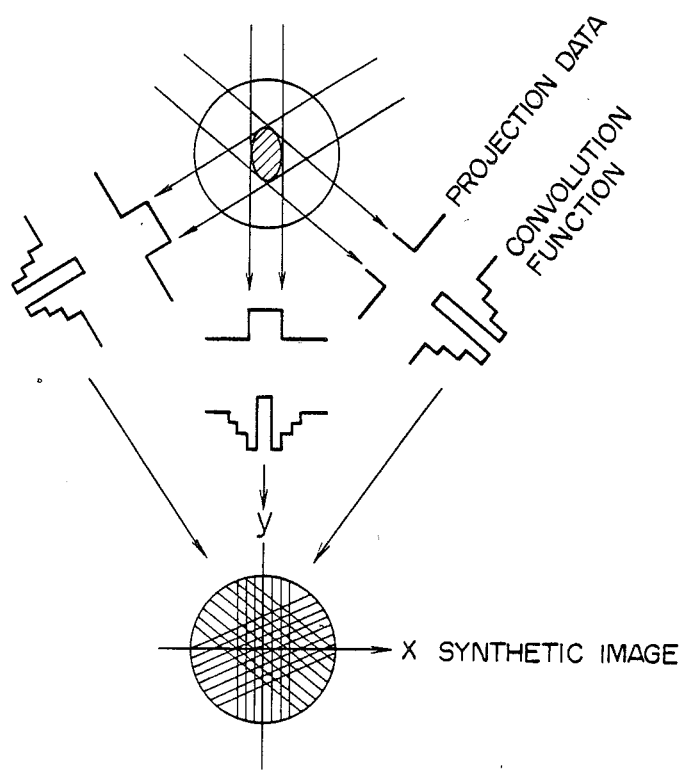
FIG. 7 is a view showing the principle of an algorithm for reconstruction of a cross section of the object.

The principle of reconstruction of a cross-sectional image using the convolution method is shown in FIG. 7 in conjunction with an example in which a collimated X-ray beam is used. Namely, a projection data function $P_0(L_0, θ_0)$ obtained by the collimated X-ray beam is correlated with a predetermined correction function to obtain a convolution function and such convolution functions for projection data from the respective directions are synthesized to obtain a cross-sectional image. This operation can be expressed by $$\mu(x, y) = \int_0^x \{P_0(L_0, θ_0) * g(L_0)\} dθ_0 \tag{3}$$

wherein * represents the convolution and g(L₀) represents the correction function. It is proved that a highly precise image can be obtained when one uses as the correction function a function expressed by the following equation (4) developed by Shepp and Logan:

$$g(na) = \frac{2}{\pi^2 a^2 (1 - 4n^2)} \quad (4)$$

wherein $L_0$ is represented by L=na (n=0, ±1, ±2, ...), a being a sampling interval at which the projection data are obtained.

Figure 8B:
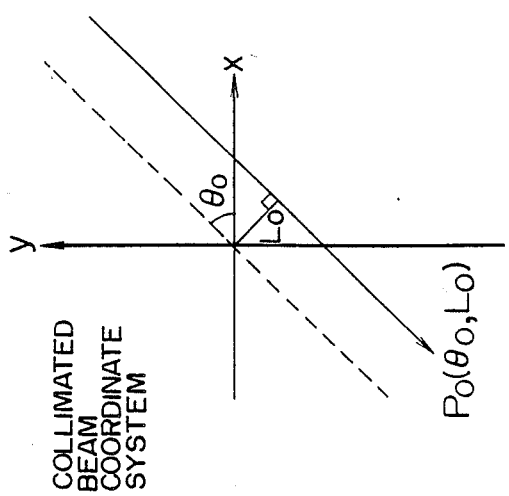
FIGS. 8a and 8b generally show a coordinate relation between detection data obtained by a fan-like beam and detection data obtained by a collimated beam.
Figure 8A:
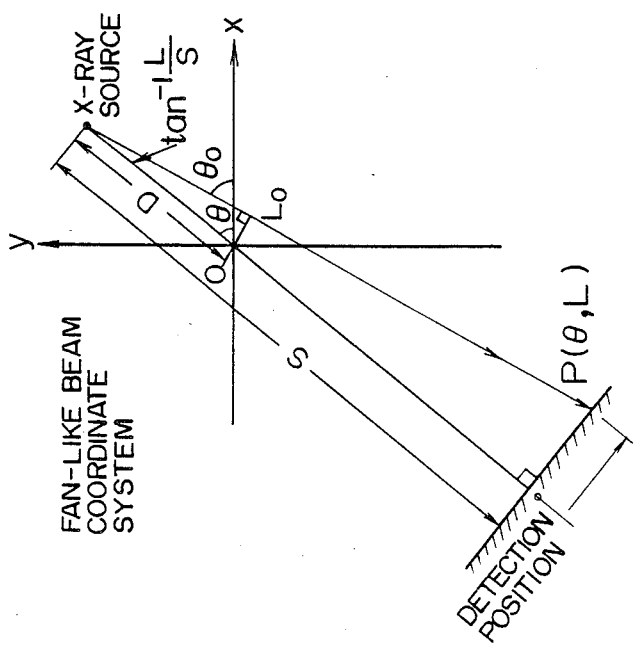

In the present embodiment, a projection data function $P(L, \theta)$ is detected by a fan-like (or sector-like) beam. Therefore, it is necessary to determine the projection data function $P_0(L_0, \theta_0)$ in a collimated beam coordinate system from the projection data function $P(L, \theta)$ in a fan-like beam coordinate system. Based on a coordinate or geometrical relation between detection data by the fan-like X-ray beam and detection data by the collimated X-ray beam as shown in FIGS. 8a and 8b, this can be achieved through a conversion according to the following equations (5) and (6):

$$\theta_0 = \theta + \tan^{-1}\frac{L}{S} \quad (5)$$

$$L_0 = D \sin \phi = D \sin (\theta - \theta_0) \quad (6)$$

wherein S represents a distance from the X-ray source to the detector and D represents a distance from the X-ray source to the rotation center of the object. The determined projection data function $P_0(L_0, \theta_0)$ in the collimated beam coordinate system is used to determine the shape of a cross section.

According to the above-explained embodiment of the present invention, the detection or imaging of a cross section of a minute object (more particularly, an object necessitating the resolution of 50 μm$^\phi$) at a predetermined position is possible. This allows the inspection of fine defects in soldered portions of an electronic circuit. Also, according to the foregoing embodiment of the present invention, the adjustment and setting of the position of a cross section of an object to be imaged can be accurately and easily carried out even if the object is very small. When the present invention is applied to the inspection of fine defects in soldered portions of an electronic circuit including LSI elements, the inspection of the defects can be made without damaging the LSI elements since the detection of an X-ray image is possible with the use of a relatively small amount of X-rays. Further, if the sequential imaging of cross sections of the soldered portions at the respective positions according to the above-described manner is carried out while step-wise moving the Y stage 3c (see FIG. 1) at a predetermined small interval, a three-dimensional image of the soldered portions can be obtained, thereby allowing the further detailed analysis of the internal structure of the soldered portions.

Figure 9:
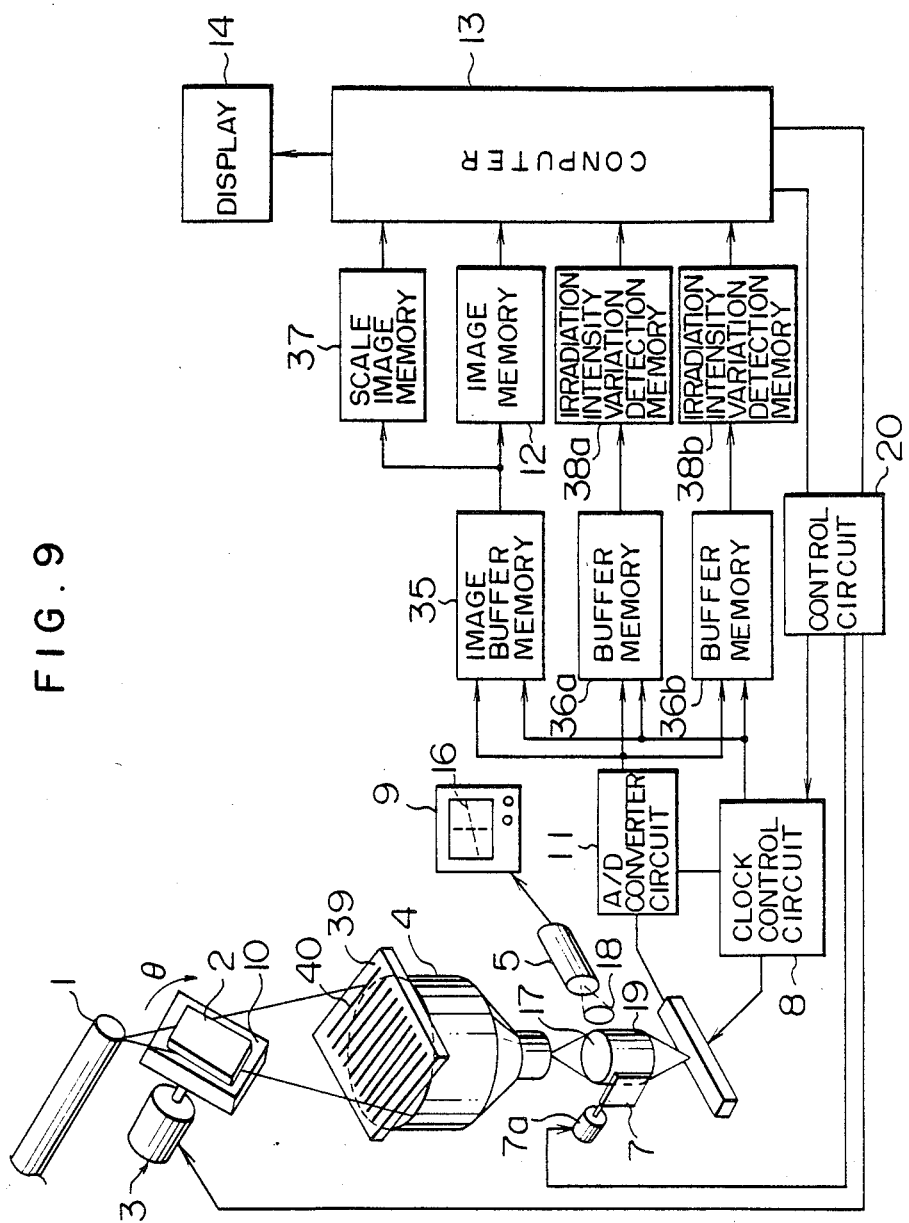
FIG. 9 is a view showing the whole construction of an X-ray tomographic imaging system according to another embodiment of the present invention.

FIG. 9 shows the whole construction of an X-ray tomographic imaging system according to another embodiment of the present invention.

Referring to FIG. 9, an object 2 held by an object holder 10 is irradiated with X-rays from an X-ray source 1 having a minute focus. An image of X-rays transmitted through the object 2 is converted by an X-ray fluorescence image intensifier 4 into a visible image and thereafter detected by a linear image sensor 6 through a relay lens 5. X-ray detection image data are outputted from the linear image sensor 6 in synchronism with a clock signal from a clock control circuit (or image detection synchronizing circuit) 8 and sequentially quantized by an A/D converter circuit 11. The quantized image data are stored into a scale image memory 37 and an image memory 12 through a buffer memory 35 and into irradiation intensity variation detection memories 38a and 38b through buffer memories 36a and 36b. Those stored data are read by a computer 13.

The object holder 10 can be rotated by a driving mechanism 3 a a pitch of Δθ in a direction of θ in accordance with a command from the computer 13.

An operation for detecting the shape of a cross section of a soldered connection portion in accordance with the present embodiment will now be explained.

Figure 10A:
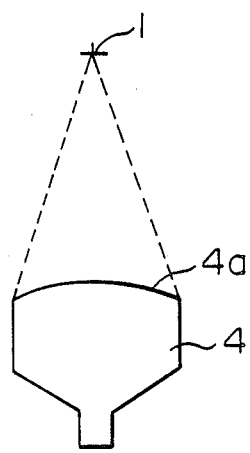
FIGS. 10a and 10b are views for explaining a geometrical distortion of an X-ray image.
Figure 10B:
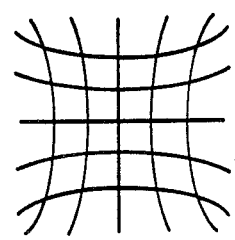
Figure 11:
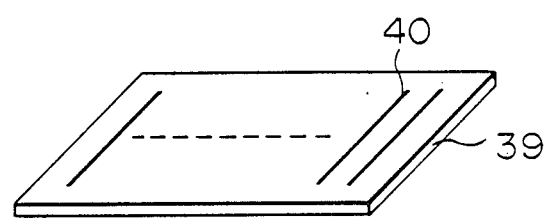
FIG. 11 is a schematic view of a scale plate used for measuring the geometrical distortion.
Figure 12A:
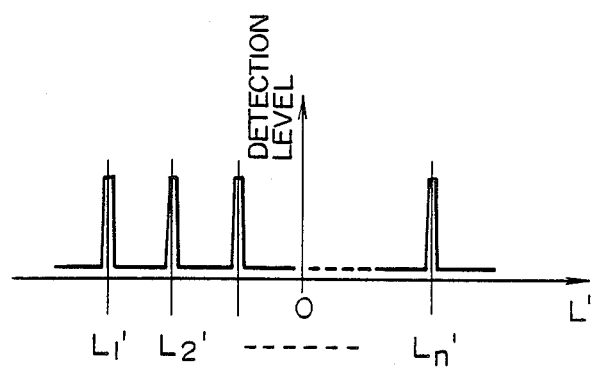
FIGS. 12a and 12b show a detection image of the scale plate and a characteristic curve for correction of the detected distortion, respectively.
Figure 12B:
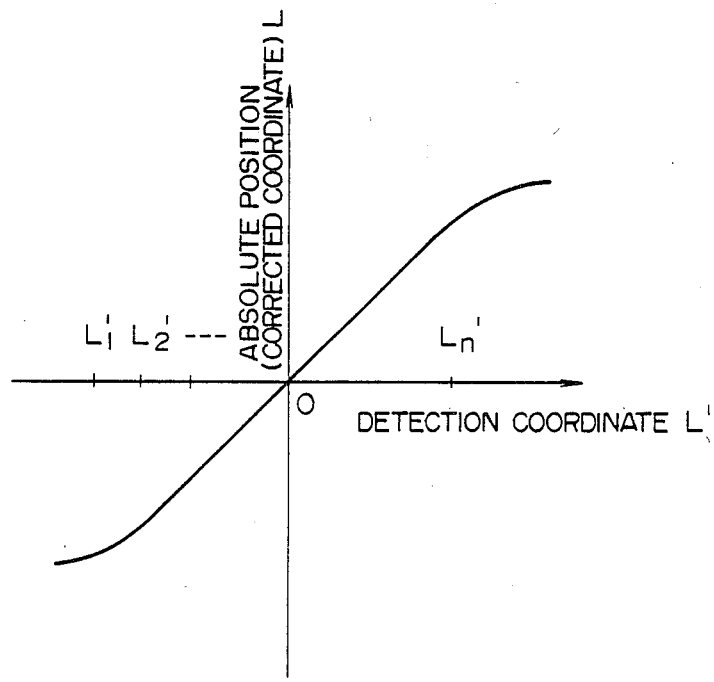

First, a scale plate including an X-ray shielding plate 39 having slits 40 provided thereon at an equal interval, as shown in FIG. 11, is placed at a detection position on a detection or X-ray receiving surface of the X-ray fluorescence image intensifier 4 at which an X-ray image of the object is projected. The detected image is stored in the scale memory 37. In general, the detection surface or X-ray receiving surface 4a of the X-ray fluorescence intensifier 4 has a spherical shape, as shown in FIG. 10a. Therefore, a detected image includes a pin-cushion-like geometrical distortion as shown in FIG. 10b. The above-mentioned scale plate detection image is used for the purpose of obtaining data for correction of this geometrical distortion. Namely, information stored in the scale image memory 32 is read by the computer 13 to determine detection coordinates $L'_1, L'_2, ---, L'_n$ of the respective slits as shown in FIG. 12a and to obtain a correction characteristic curve of the detection coordinate r' with respect to the absolute position r as shown in FIG. 12b. The correction characteristic curve is used for correcting the geometrical distortion of the object detection image.

Next, the object 2 set on the object holder 10 is placed to a position at which the inspection of the object is to be made, as shown in FIGS. 13a and 13b. Thereafter, while the object holder 10 is intermittently rotated by the driving mechanism 3 at the pitch of Δθ in the θ direction, X-ray projection images $I(L', \theta)$ of the object are sequentially stored in the image memory 12. L' represents a detection position on the linear image sensor 6. At the same time, as shown in FIG. 13a, irradiation X-rays which do not pass through the object are detected as $I_0(L'_a, \theta)$ and $I_0(L'_b, \theta)$ by X-ray receiving elements 61a and 61b on the linear image sensor 6, as shown in FIG. 13a, $I_0(L'_a, \theta)$ and $I_0(L'_b, \theta)$ are stored in the irradiation intensity variation detection memories 35a and 35b, respectively.

Further, in order to detect the distribution $I_0(L')$ of intensities of the irradiation X-rays, the intensity of X-rays directly irradiated in a state in which the object is removed is detected by the linear image sensor 6 and stored in the image memory 12. At the same time, the values of intensities detected by the X-ray receiving elements 61a and 61b are stored in the irradiation intensity variation detection memories 35a and 35b, respectively.

FIG. 6 shows an example of image data $I(L, \theta)$ after the correction of a geometrical distortion has been made for X-ray image detection data $I(L', \theta)$ detected corresponding to the rotation angle of the object in the θ direction.

Next, explanation will be made of a method for using those detection data to reconstruct the shape of a cross section of the object through an operation by the computer 13.

Assuming that the distribution of X-ray absorption coefficients of the object is $\mu(x, y)$, the image data $I(L, \theta)$ can be expressed by the following equation:

$$I(L, \theta) = I_0 e^{-\int \mu(x, y)dl} \qquad (7)$$

wherein $\int \mu(x, y)dl$ is the value of integration of X-ray absorption coefficients $\mu(x, y)$ at passing positions of an X-ray beam and $I_0$ represents the intensity of irradiation X-rays. The equation (7) can be rewritten as follows:

$$\int \mu(x, y)dl = \ln \{I_0/I(L, \theta)\} \qquad (8)$$

The reconstruction of a cross-sectional image includes introducing the measured image data $I(L, \theta)$ into the equation (8) to determine the distribution of X-ray absorption coefficients $\mu(x, y)$. However, it should be noted that the introduced irradiation X-ray intensity $I_0$ may have a different distribution depending on the detection position L and may vary with the lapse of time, thereby resulting in a factor of error in an operation processing. Therefore, in the present embodiment, a correction of this variation with the lapse of time is further made for the coordinate correction data $I_0(L, \theta)$ of the irradiation X-ray intensity distribution $I_0(L', \theta)$ measured by the above-described method. Namely, the above-mentioned variation amount detection values $I_0(L_a', \theta)$ and $I_0(L_b', \theta)$ are used to determine the following corrected value $I_0$:

$$I_0 = I_0(L, \theta) \times \frac{I_0(L_a', \theta) + I_0(L_b', \theta)}{I_0(L_a') + I_0(L_b')} \qquad (9)$$

Accordingly, the equation (8) can be rewritten as follows:

$$\int \mu(x, y)dl = \ln\left(\frac{I_0(L, \theta)}{I(1, \theta)} \cdot \frac{I_0(L_a', \theta) + I_0(L_b', \theta)}{I_0(L_a') + I_0(L_b')}\right) \qquad (10)$$
$$= P(L, \theta)$$

wherein $P(L, \theta)$ is called projection data.

Various methods of determining $\mu(x, y)$ from the projection data $P(L, \theta)$ are known. An example based on a convolution method will be briefly explained hereinbelow.

The principle of reconstruction as illustrated in shown in FIG. 7 in which a collimated X-ray beam is used, includes correlating a predetermined filter function with projection data $P_0(L_0, \theta_0)$ obtained by the collimated beam to obtain a convolution function for the projection data from each direction. Next, such convolution functions are synthesized to obtain a cross-sectional image. This operation can be expressed by $$\mu(x, y) = \int_0^\pi d\theta_0 \int_{L_{0min}}^{L_{0max}} \{P_0(L_0 - \tau, \theta_0) \cdot g(L_0)\}d\tau \qquad (11)$$

wherein $L_{0\,min}$ and $L_{0\,max}$ are the minimum and maximum values of a coordinate range in which the projection data are obtained, and $g(L_0)$ represents the filter function. It is proved that an image with high precision can be obtained if one uses as the filter function $g(L_0)$ a function represented by the following equation (12) developed by Shepp and Logan:

$$g(L_0) = \frac{1}{\pi^2 a^2 (1 - 4n^2)} \qquad (12)$$

wherein $L_0$ is represented by $L_0 = na$ ($n = 0, \pm 1, \pm 2 \ldots$), a being a sampling interval at which the projection data are obtained.

In the present embodiment, since the projection data $P(L, \theta)$ are detected by a fan-like beam (or sector-like beam), it is necessary to determine projection data $P_0(L_0, \theta_0)$ in a collimated beam coordinate system from $P(L, \theta)$. This can be achieved by using the conversion equations (5) and (6) which have already ben described. The determined projection data $P_0(L_0, \theta_0)$ are used to reconstruct the shape of a cross section.

According to the above-described embodiment, the detection of a cross-sectional image with a high precision and a high resolution is possible without any influences of the geometrical distortion in the detection image by the X-ray fluorescence image intensifier and the variation in intensity of the irradiation X-rays. Therefore, there can be realized the inspection of fine defects in soldered portions of an electronic circuit.

We claim:

1. An X-ray tomographic imaging system comprising:
    an X-ray source irradiating an object to be inspected with X-rays to obtain an X-ray transmission image thereof;
    means for converting said transmission image into a detection light image and intensifying the intensity of said detection light image;
    photo-electric converter converting said light image from said means for converting into an electrical signal;
    an object holder holding said object rotatably at position in proximity to said X-ray source and movably in a first direction along the axis of rotation of said object holder and in a second direction perpendicular to said first direction of the rotation axis;
    means for detecting an image signal from said detection light image;
    means for displaying said image signal;
    means for adjusting a relative position between a visual field detected by said photo-electric converter and a detected cross-sectional position of the object on the basis of said image signal displayed on the means for displaying;
    an analog to digital converter circuit sequentially quantizing the electrical signals from said photoelectric converter for each predetermined rotation angle $\Delta\theta$ of the object holder for a plurality of directions and an image memory storing the quantized electrical signals to obtain data; and
    a computer reconstructing an image of a cross section of the object by processing said data for a plurality directions.

2. An X-ray tomographic imaging system according to claim 1, further comprising means for correcting a geometrical distortion in said detection light images produced by said converting means.

3. An X-ray tomographic imaging system according to claim 1, further comprising a linear image sensor, wherein in sequentially detecting X-ray images of said object from a plurality of directions, said linear image sensor detects the intensities of directed incident X-rays which do not pass through said object, such that data of the detected intensities of directly incident X-rays are used to correct the distribution of intensities of irradiation X-rays when the X-ray images are detected.

4. An X-ray tomographic imaging system according to claim 1, wherein said object to be inspected includes a portion at which an LSI chip is soldered to a substrate.

5. An X-ray tomographic imaging system according to claim 1, wherein said means for converting includes an X-ray fluorescence image intensifier.

6. An X-ray tomographic imaging system comprising:
   an X-ray source having a minute spot size;
   first means for detecting an enlarged projected X-ray transmission image of an object which is to be inspected and irradiated with X-rays from said X-ray source and converting said transmission image into a detection image and intensifying the amount of light of said detection image;
   a linear image sensor receiving an output image of said first means to convert it into an electrical signal;
   second means for reconstructing the image of a cross section of said object on the basis of an output signal of said linear image sensor;
   a scale including a plate which is made of a material having an X-ray shielding characteristic and is provided with slit-like graduations thereon; and
   third means for detecting an X-ray image obtained by the irradiation of said scale with X-rays from said X-ray source and storing data of the detected X-ray image, such that upon detection of an X-ray image, the stored data are read to correct a geometrical distortion in an X-ray detection image produced by said first means.

7. An X-ray tomographic imaging system according to claim 6, wherein said object to be inspected includes a portion at which an LSI chip is soldered to a substrate.

8. An X-ray tomographic imaging system according to claim 6, further comprising a linear image sensor, wherein in sequentially detecting X-ray images of said object from a plurality of directions, said linear image sensor detects the intensities of directly incident X-rays which do not pass through said object such that data of the detected intensities of directly incident X-rays are used to correct the distribution of intensities of irradiation X-rays when the X-ray images are detected.

9. An X-ray tomographic imaging system according to claim 6, wherein said first means includes an X-ray fluorescence image intensifier.

10. An X-ray tomographic imaging system comprising:
    means for irradiating an object to be inspected with x-rays;
    means for converting an X-ray transmission image of said object irradiated with the X-rays into a light image;
    a sensor for picking up said light image obtained by said means for converting;
    means for changing the posture of said object;
    means for picking up a two-dimensional X-ray image of said object to display a monitor image;
    means for adjusting a relative positional relationship between said object and said sensor; and
    means for performing a remote control of said means for adjusting to adjust a display position of said means for displaying which is displayed on said means for picking up in an interlocking manner with the movement of said sensor, such that X-ray images from a plurality directions are detected on the basis of a video signal from said sensor to obtain an image of a cross section of said object.

11. An X-ray tomographic imaging system according to claim 10, wherein said object to be inspected includes a portion at which an LSI chip is soldered to a substrate.

12. An X-ray tomographic imaging system according to claim 1, wherein said means for converting includes an X-ray fluorescence image intensifier.

13. An X-ray tomographic imaging method comprising the steps of:
    holding an object with a plurality of soldering portions at which an LSI chip is soldered to a multilayer substrate which has through-holes filled with a metal material and circuit wirings made of a metal material on an object holder;
    irradiating an X-ray from an X-ray source directly to said soldering portions from a peripheral direction of a side face of the chip to obtain an X-ray transmission image thereof;
    converting said transmission image into a detection light image and intensifying the intensity of said detection light image;
    converting said light image into an electrical signal by a photo-electric converter of the soldering portions;
    displaying a visual transmission image of the solder portions
    adjusting a relative position between said visual image selected by said photo-electric converter and a detected cross-sectional position of the soldering portions;
    rotating the object through a plurality rotation angle positions displaced by $\Delta\theta$;
    obtaining electrical signals from each of the rotation angle positions;
    processing said electrical signals obtained at said rotation angle positions; and
    displaying a cross-sectional image of the soldering portions using said processed electrical signals.

14. An X-ray tomographic imaging method according to claim 13, wherein said X-ray source that has a minute spot size is used and an X-ray fluorescene image intensifier is used to convert said transmission image into a detection light image.

* * * * *

UNITED STATES PATENT AND TRADEMARK OFFICE
CERTIFICATE OF CORRECTION

PATENT NO. : 4,872,187

DATED : October 3, 1989

INVENTOR(S) : K. Nakahata, et al.

It is certified that error appears in the above-identified patent and that said Letters Patent is hereby corrected as shown below:

Column 1, lne 21, change "its" to --a--.

Column 2, line 20, delete the comma after "has".

Column 3, line 8, change "florescence" to --fluorescence--.

Column 3, line 55, change "s" to --is--.

Column 5, line 14, delete "that" between "course" and "the".

Column 6, line 26, change "o" to --a--.

Column 6, line 36, between "of" and "shape" insert --)--.

Column 6, line 57, between "of" and "showing" insert --the object--.

Column 6, line 61, change "as" to --of--.

UNITED STATES PATENT AND TRADEMARK OFFICE
CERTIFICATE OF CORRECTION

PATENT NO. : 4,872,187

DATED : October 3, 1989

INVENTOR(S) : K. Nakahata, et al.

It is certified that error appears in the above-identified patent and that said Letters Patent is hereby corrected as shown below:

Column 8, line 28, change "...).e..." to --...)·e...--.

Column 10, line 11, change "a a pitch" to --at a pitch--.

Column 11, lines 6 and 7, "image data..." on line 7 should continue on line 6 right after "...y), the".

Column 11, line 52, change "in" to --is--.

Column 12, line 16, change "ben" to --been--.

Column 12, line 60, after "plurality" insert --of--.

Column 14, line 16, after "plurality" insert --of--.

UNITED STATES PATENT AND TRADEMARK OFFICE
CERTIFICATE OF CORRECTION

PATENT NO. : 4,872,187
DATED : October 3, 1989
INVENTOR(S) : K. Nakahata, et al.

It is certified that error appears in the above-identified patent and that said Letters Patent is hereby corrected as shown below:

Column 14, line 48, insert --of-- between "plurality" and "rotation".

Signed and Sealed this

Twelfth Day of February, 1991

Attest:

HARRY F. MANBECK, JR.

*Attesting Officer*  *Commissioner of Patents and Trademarks*